US012690602B2

(12) United States Patent
Liu et al.

(10) Patent No.: US 12,690,602 B2
(45) Date of Patent: Jul. 28, 2026

(54) TRADITIONAL CHINESE MEDICINE POLYSACCHARIDE EXTRACT FREEZE-DRYING PROTECTIVE AGENT, DIRECT-TO-VAT STARTER AND PREPARATION METHODS THEREOF

(71) Applicant: Freshwater Fisheries Research Institute of Jiangsu Province, Nanjing (CN)

(72) Inventors: Chongwan Liu, Nanjing (CN); Xiaohua Zhu, Nanjing (CN); Hongsheng Yang, Nanjing (CN); Yong Meng, Nanjing (CN); Zhihua Xu, Nanjing (CN); Di Ren, Nanjing (CN)

(73) Assignee: Freshwater Fisheries Research Institute of Jiangsu Province, Nanjing (CN)

( * ) Notice: Subject to any disclaimer, the term of this patent is extended or adjusted under 35 U.S.C. 154(b) by 630 days.

(21) Appl. No.: 18/092,455

(22) Filed: Jan. 3, 2023

(65) Prior Publication Data

US 2023/0148629 A1 May 18, 2023

(30) Foreign Application Priority Data

Jan. 26, 2022 (CN) .......................... 202210091805.6

(51) Int. Cl.
| | |
|---|---|
| A23K 10/12 | (2016.01) |
| A23K 10/30 | (2016.01) |
| A23K 20/105 | (2016.01) |
| A23K 20/142 | (2016.01) |
| A23K 20/163 | (2016.01) |
| A23K 50/80 | (2016.01) |
| C12N 1/04 | (2006.01) |
| C12N 1/16 | (2006.01) |
| C12N 1/20 | (2006.01) |

(52) U.S. Cl.
CPC .............. *A23K 10/12* (2016.05); *A23K 10/30* (2016.05); *A23K 20/105* (2016.05); *A23K 20/142* (2016.05); *A23K 20/163* (2016.05);
*A23K 50/80* (2016.05); *C12N 1/04* (2013.01); *C12N 1/16* (2013.01); *C12N 1/20* (2013.01)

(58) Field of Classification Search
CPC ..................................................... A23K 20/137
See application file for complete search history.

(56) References Cited

U.S. PATENT DOCUMENTS

| | | | |
|---|---|---|---|
| 2003/0165472 A1* | 9/2003 | McGrath | .................. A01K 7/02 |
| | | | 424/93.4 |
| 2016/0298077 A1* | 10/2016 | Salmons | ................ A01N 1/125 |
| 2019/0225631 A1 | 7/2019 | Yano et al. | |
| 2019/0374586 A1 | 12/2019 | Kawaguchi et al. | |
| 2020/0325163 A1 | 10/2020 | Yano et al. | |
| 2021/0196778 A1* | 7/2021 | Xiao | .................... A61K 36/076 |

OTHER PUBLICATIONS

Zhang et al. (CN 109924413) Machine Translation (Year: 2019).*
Yang et al. CN 106036040 Machine Translation (Year: 2016).*
Jia et al. CN-102524518-A Machine Translation (Year: 2012).*

* cited by examiner

*Primary Examiner* — Felicia C Turner
(74) *Attorney, Agent, or Firm* — Hemisphere Law, PLLC

(57) ABSTRACT

A traditional Chinese medicine polysaccharide extract freeze-drying protective agent, a direct-to-vat starter and preparation methods thereof are disclosed, which belong to the technical field of feed starter. The compound traditional Chinese medicine polysaccharide extract freeze-drying protective agent includes *Poria cocos* polysaccharide extract, *Atractylodes macrocephala* polysaccharide extract, *Radix codonopsis* polysaccharide extract, L-tyrosine, α-cyclodextrin and polyethyleneimine. Its application in the freeze-drying protection of direct-to-vat starter of aquatic fermentation feed can reduce the damage to the cells caused by freeze-drying, improve the survival rate of the cells in the starter after freeze-drying, effectively prolong the storage period of the starter, and ensure that the fermentation activity remains at a high level during storage.

4 Claims, No Drawings

TRADITIONAL CHINESE MEDICINE POLYSACCHARIDE EXTRACT FREEZE-DRYING PROTECTIVE AGENT, DIRECT-TO-VAT STARTER AND PREPARATION METHODS THEREOF

CROSS REFERENCE TO RELATED APPLICATION

This patent application claims the benefit and priority of Chinese Patent Application No. 202210091805.6, filed on Jan. 26, 2022, the disclosure of which is incorporated by reference herein in its entirety as part of the present application.

TECHNICAL FIELD

The present disclosure relates to the technical field of feed starter, and more specifically, to a traditional Chinese medicine polysaccharide extract freeze-drying protective agent, a direct-to-vat starter and preparation methods thereof.

BACKGROUND ART

Fermented feed can regulate the microecological balance in aquatic animals, promote the healthy growth of animals, improve production performance, reduce costs and increase efficiency, regulate and protect the ecological environment of water bodies, and meet the development requirements of healthy and environment friendly fisheries. It has broad market application prospects.

In the preparation of fermented feed at present, the production strain in the dormant state is usually made into a liquid starter through the processes of activation, multiple expansion and culture, and then inoculated with feed raw materials for fermentation. Before the production of each batch of feed, the preparation process of liquid starter needs to be repeated. The process is cumbersome, requires high skills for fermentation equipment and technicians. The transportation cost of liquid starter is high. The vitality of the strain is easy to deteriorate.

Based on the problems of liquid starter, the direct-to-vat solid starter came into being. After high-density culture and cell concentration and separation, the strain is mixed with the protective agent to obtain the strain suspension. Finally, the high concentration and standardized direct-to-vat starter is prepared by drying and aseptic packaging. In actual production, activation, expansion, culture and other processes are no longer needed, and it is directly put into use. It has the advantages of small volume, convenient carrying, omitting the preparation process of the starter before production, and reducing the investment in the strain workshop. Moreover, it can effectively prevent the degradation and pollution of the strain, and has high fermentation vitality and long storage period, which can greatly improve the labor productivity and product quality of fermentation production.

At present, drying is the key problem that restricts the large-scale promotion of direct-to-vat fermentation. Common strain drying methods include spray drying, vacuum low-temperature drying and vacuum freeze-drying. Among them, the first two methods are limited due to serious damage to the cells, low activity of the prepared strains and difficulty in long-term preservation. Vacuum freeze-drying has become the mainstream drying method. First, the sample is frozen at low temperature (the water in the sample freezes into ice), and then the ice crystals sublimate under vacuum conditions to remove water, so as to ensure that the sample reaches a dry state. However, if vacuum freeze-drying is carried out directly, it will inevitably cause certain degree of damage to the cells, reduce the survival rate of cells and cell vitality, and affect its fermentation performance. The addition of freeze-drying protective agent in the strains can effectively change the physical and chemical environment of biological samples during freeze-drying, reduce or prevent the damage to cells caused by freeze-drying or rehydration, and maintain the original physiological and biochemical characteristics and biological activity of cells as much as possible. Therefore, the screening of freeze-drying protective agents is the core issue in the preparation of high activity direct-to-vat starter. However, the existing microbial freeze-drying protective agents have poor protection effect on the cells, resulting in low viability of the strains, especially after storage for a period of time, the fermentation vitality of the strains decreases, and the startup fermentation speed of the strains is slow.

Therefore, how to reduce the impact of the freeze-drying process on the cells and ensure the fermentation vitality of the direct-to-vat starter is a technical problem to be solved in the field.

SUMMARY

The disclosure provides a traditional Chinese medicine polysaccharide extract freeze-drying protective agent, a direct-to-vat starter and preparation methods thereof, which can effectively reduce the damage to the cells caused by freeze-drying.

In order to achieve the above purpose, technical solutions of the present disclosure are specifically described as follows.

The compound traditional Chinese medicine polysaccharide extract freeze-drying protective agent is made from following raw materials: *Poria cocos* polysaccharide extract, *Atractylodes macrocephala* polysaccharide extract, *Radix codonopsis* polysaccharide extract, L-tyrosine, α-cyclodextrin and polyethyleneimine.

After the freeze-drying protective agent of the present disclosure is combined with water molecules, the viscosity of the solution is increased, the crystallization process of water is weakened, the damage of solute is reduced, and the permeability and integrity of the cell membrane are maintained, thus the effect of protecting the cells is achieved. Its application in the protection of the direct-to-vat starter for aquatic fermentation feed can reduce the damage to the cells caused by freeze-drying, improve the survival rate of the cells in the starter after freeze-drying, effectively prolong the storage period of the starter, and ensure that the fermentation activity remains at a high level during storage.

Further, the compound traditional Chinese medicine polysaccharide extract freeze-drying protective agent is made from following raw materials: *Poria cocos* polysaccharide extract 10.0~30.0 g/100 mL, *Atractylodes macrocephala* polysaccharide extract 10.0~20.0 g/100 mL, *Radix codonopsis* polysaccharide extract 5.0~20.0 g/100 mL, L-tyrosine 2.0~10.0 g/100 mL, α-cyclodextrin 2.0~7.0 g/100 mL and polyethyleneimine 2.0~5.0 g/100 mL.

The preparation method of the compound traditional Chinese medicine polysaccharide extract freeze-drying protective agent includes the following steps.

(1) Alkalization, etherification, ethanol precipitation and drying are performed on *Poria cocos* powder to obtain *Poria cocos* polysaccharide extract.

(2) Ethanol extraction, ultrasonic extraction and drying are performed on *Atractylodes macrocephala* powder to obtain *Atractylodes macrocephala* polysaccharide extract.

(3) Microwave extraction, ethanol precipitation and drying are performed on *Radix codonopsis* powder to obtain *Radix codonopsis* polysaccharide extract.

(4) The *Poria cocos* polysaccharide extract, *Atractylodes macrocephala* polysaccharide extract and *Radix codonopsis* polysaccharide extract are mixed in water, and the solution A is obtained after sterilization.

(5) The L-tyrosine, α-cyclodextrin and polyethyleneimine are mixed in water, and the solution B is obtained after sterilization.

(6) The solution A and the solution B are mixed to obtain the freeze-drying protective agent.

Further, in step (1),

*Poria cocos* powder is screened through 100~150 meshes;

the alkalization includes: adding NaOH solution into *Poria cocos* powder, continuously stirring until the *Poria cocos* powder is completely dissolved to obtain *Poria cocos* alkalinization solution; wherein 200~400 mL NaOH solution is added to every 100 g of *Poria cocos* powder, and the mass fraction of the NaOH solution is 40~60%;

the etherification includes: adding chloroacetic acid to the *Poria cocos* alkalization solution, continuously stirring, reacting at 45~65° C. for 6~8 h to obtain *Poria cocos* etherification solution; wherein for every 100 g of *Poria cocos* powder, 40~100 g of the chloroacetic acid solid is added in batches;

the ethanol precipitation includes: adding 95% ethanol-acetic acid solution to the *Poria cocos* etherification solution for precipitation, redissolving the precipitate with water, then using ethanol solution with mass fraction of 95% for ethanol precipitation, and collecting the precipitate;

the volume ratio of 95% ethanol-acetic acid solution to *Poria cocos* etherification solution is 3:1 to 5:1, and the 95% ethanol-acetic acid solution is prepared by mixing ethanol solution with mass fraction of 95% and acetic acid with mass fraction of 95% in the volume ratio of 1:1; and the drying includes: drying the precipitate obtained in the ethanol precipitation step by means of vacuum drying at 35~45° C. for 4~6 h.

Further, in step (2),

*Atractylodes macrocephala* powder is screened through 100~150 meshes;

the ethanol extraction incudes: adding ethanol solution into the *Atractylodes macrocephala* powder, heating and refluxing at 80~85° C. for 2~3 h, and filtering to obtain *Atractylodes macrocephala* granules; wherein the mass fraction of the ethanol solution is 70~75%, and the dosage is calculated by adding 20 mL ethanol solution per gram of *Atractylodes macrocephala* powder;

the ultrasonic extraction includes: adding distilled water to the *Atractylodes macrocephala* granules, extracting them by ultrasonic at 75~80° C. for 60~90 min to obtain a filtrate, and filtering the filtrate for standby; and the drying includes: vacuum freeze-drying the filtrate, wherein the filtrate is prefrozen at −20~−35° C. for 5-8 h before freeze-drying.

Further, in step (3),

*Radix codonopsis* powder is screened through 100~150 meshes;

the microwave extraction includes: after soaking *Radix codonopsis* powder with water for 8-12 h, performing heating reaction in a microwave reactor at 200~260° C. for 1~1.5 h, filtering to obtain *Radix codonopsis* microwave extraction solution; wherein 1000~2000 mL water is added into every 100 g of *Radix codonopsis* powder;

the ethanol precipitation includes: adding 3-5 times volume of ethanol into the *Radix codonopsis* microwave extraction solution for ethanol precipitation, standing for 6-8 h, centrifuging for 10-15 min at 4000 r/min, adding sewage reagent after removing the supernatant, swirling and mixing evenly, and then centrifuging for 10-15 min at 5000 r/min, subjecting the supernatant obtained by centrifugation to secondary ethanol precipitation and precipitate collection; wherein the sewage reagent is prepared from trichloromethane and n-butanol according to a volume ratio of 4:1; and the drying includes: drying the precipitate obtained in the ethanol precipitation step by means of vacuum drying at 35~45° C. for 4~6 h.

The freeze-drying protective agent can be applied to freeze-drying protection of microorganisms used for production of aquatic fermented feed.

The direct-to-vat starter includes the above compound traditional Chinese medicine polysaccharide extract freeze-drying protective agent, *Enterococcus faecalis, Candida utilis, Aspergillus niger, Bacillus coagulans* and *Brevibacillus laterosporus*.

The preparation method of the direct-to-vat starter includes the following steps. The mixed strain solution of *Enterococcus faecalis, Candida utilis, Aspergillus niger, Bacillus coagulans* and *Brevibacillus laterosporus* is mixed with the freeze-drying protective agent according to the volume ratio of 1:1 to 1:4, and the freeze-drying is carried out to obtain the direct-to-vat starter.

Further, in the mixed strain solution, the viable concentration of *Enterococcus faecalis* is $1.0 \times 10^{10}$~$6.0 \times 10^{10}$ CFU/mL;

the viable concentration of *Candida utilis* is $3.0 \times 10^{8}$~$6.0 \times 10^{8}$ CFU/mL;

the viable concentration of *Aspergillus niger* is $8.0 \times 10^{7}$~$2.0 \times 10^{8}$ CFU/mL;

the viable concentration of *Bacillus coagulans* is $5.0 \times 10^{7}$~$3.0 \times 10^{8}$ CFU/mL; and the viable concentration of *Brevibacillus laterosporus* is $1.0 \times 10^{8}$~$4.0 \times 10^{8}$ CFU/mL.

Further, the preparation method of the mixed strain solution of *Enterococcus faecalis, Candida utilis, Aspergillus niger, Bacillus coagulans* and *Brevibacillus laterosporus* includes the following steps.

(1) The various strains are activated.

(2) After the activation, all strains are mixed for multiplication culture, the culture solution is centrifuged and resuspension is performed with physiological saline to obtain the mixed strain solution.

The multiplication medium used in the process of multiplication culture is composite medium of Jerusalem artichoke and *Poria cocos*.

The preparation method of the composite culture medium of Jerusalem artichoke and *Poria cocos* includes: mixing Jerusalem artichoke powder, *Poria cocos* water extract and water at a mass ratio of 2:3:5, hydrolyzing at 65° C. for 60 min, heating to 95° C. and hydrolyzing for 60 min, cooling, filtering with 8 layers of gauze, and adjusting pH value of the filtrate to 7.0~7.3 to obtain the composite culture medium of Jerusalem artichoke and *Poria cocos*;

The preparation method of the Jerusalem artichoke powder includes: slicing fresh Jerusalem artichoke, drying the fresh Jerusalem artichoke slices at 70~80° C. until the water content is lower than 8%, and then crushing the dried Jerusalem artichoke slices and sieving the crushed Jerusalem artichoke slices through 100 meshes to obtain the Jerusalem artichoke powder.

The preparation method of the *Poria cocos* water extract includes: slicing fresh *Poria cocos*, drying the fresh *Poria cocos* slices at 70~80° C., and then crushing the dried *Poria cocos* slices; adding 10~15 times the mass of absolute ethanol, extracting for 2~4 h and subjecting the extract to filtering to obtain a residue; adding 8~10 times the mass of distilled water to the residue, heating and refluxing to extract for 2 h, filtering twice to obtain filtrates, combining the filtrates, subjecting the combined filtrate to concentrating and drying under reduced pressure to obtain the *Poria cocos* water extract.

Further, the activation process of each strain is as follows.

The slants of all strains are inoculated with the primary seed medium, and the primary seed solution is obtained after culture, and the primary seed solution is further activated and expanded for culture to obtain the secondary seed solution.

The activating conditions of *Enterococcus faecalis* strain are as follows. The primary seed culture conditions are 32~35° C., 48 hours. The inoculation amount of secondary seeds is 0.5%~2%, the culture condition is 32~35° C., the shaking table culture is 120~480 r/min for 18~24 hours, and the seeds are stored at 4° C. for standby.

The activating conditions of *Candida utilis* strain are as follows. The primary seed culture conditions are 25~28° C., 48 hours. The inoculation amount of secondary seeds is 3.0%~7.0%, the culture condition is 25~28° C., the shaking table culture is 120~480 r/min for 18~24 hours, and the seeds are stored at 4° C. for standby.

The activating conditions of *Aspergillus niger* strain are as follows. The primary seed culture conditions are 30~35° C., 20 hours. The inoculation amount of secondary seeds is 3.0%~7.0%, the culture condition is 32~35° C., the shaking table culture is 120~480 r/min for 12~48 hours, and the seeds are stored at 4° C. for standby.

The activating conditions of *Bacillus coagulans* strain are as follows. The primary seed culture conditions are 45~55° C., 16 hours. The inoculation amount of secondary seeds is 1.0%~3.0%, the culture condition is 45~55° C., the shaking table culture is 120~180 r/min for 12~18 hours, and the seeds are stored at 4° C. for standby.

The activating conditions of *Brevibacillus laterosporus* strain are as follows. The primary seed culture conditions are 20~40° C., 24 hours. The inoculation amount of secondary seeds is 2.0%~5.0%, the culture condition is 20~40° C., the shaking table culture is 120~180 r/min for 24~32 hours, and the seeds are stored at 4° C. for standby.

The composition of primary and secondary seed culture media of *Enterococcus faecalis, Candida utilis, Aspergillus niger, Bacillus coagulans* and *Brevibacillus laterosporus* is as follows. Every 100 mL of the media contains 1.0~2.0 g of yeast powder, 2.0~3.0 g of beef extract, 2.5~4.5 g of tryptone, 0.1~0.2 g of sodium bicarbonate, 1.8~3.6 g of glucose, 0.1~0.3 g of sodium chloride, 0.1~0.2 g of sodium acetate, 0.015~0.020 g of magnesium sulfate and 0.005~0.008 g of manganese sulfate.

Further, in the freeze-drying step, the prefreezing process is carried out for 3 h at −80° C., and the strain solution is quickly transferred to a vacuum freeze-drying machine for freeze-drying after being completely frozen. The freeze-drying conditions are vacuum degree 10 Pa and cold trap temperature −55° C. And a setting procedure of diaphragm temperature is heating for 2 h at 10° C., heating for 3 h at 20° C., heating at 30° C., and freeze-drying for 20 h.

The direct-to-vat starter or the direct-to-vat starter prepared by the above method is applied to the preparation of aquatic fermentation feed, which can ensure the fermentation vitality, and thus help to ensure the stability of production of aquatic fermentation feed and product quality.

In summary, the freeze-drying protective agent of the disclosure has simple composition and low cost, can reduce the damage of freeze-drying to concentrated cells, improve the survival rate of cells in the starter after freeze-drying, and can effectively prolong the storage period of the starter, which is suitable for long-term storage of strains. The direct-to-vat starter prepared with the freeze-drying protective agent has high strain survival rate, high fermentation performance, fast start-up fermentation speed, and ensures that the fermentation activity is maintained at a high level during storage. After 150 days of storage at low temperature, the viable count and fermentation performance have no significant difference from that of liquid fermentation. It is suitable for the production of aquatic fermentation feed and is conducive to improving the safety and stability of feed quality.

DETAILED DESCRIPTION OF THE EMBODIMENTS

Technical solutions of the present disclosure will be clearly and completely described below with reference to the embodiments. Obviously, the described embodiments are only part of the embodiments of the present disclosure, not all of them. Based on the embodiments of the disclosure, all other embodiments made by those skilled in the art without sparing any creative effort should fall within the protection scope of the disclosure.

Embodiment 1

A freeze-drying protective agent included the following components: *Poria cocos* polysaccharide extract 10.0 g/100 mL, *Atractylodes macrocephala* polysaccharide extract 10.0 g/100 mL, *Radix codonopsis* polysaccharide extract 5.0 g/100 mL, L-tyrosine 2.0 g/100 mL, α-cyclodextrin 2.0 g/100 mL and polyethyleneimine 2.0 g/100 mL.

The preparation method of the freeze-drying protective agent included the following steps.

(1) *Poria cocos* decoction pieces were crushed with a common Chinese herbal medicine pulverizer and sieved through 100 meshes to obtain *Poria cocos* powder.

Alkalization: NaOH solution was added to the *Poria cocos* powder and continuously stirred until the *Poria cocos* powder was completely dissolved to obtain *Poria cocos* alkalization solution. 200 mL of NaOH solution was added to every 100 g of *Poria cocos* powder, and the mass fraction of NaOH solution was 50%.

Etherification: chloroacetic acid solid (domestic analytical pure) was slowly added to the *Poria cocos* alkalization solution in batches and continuously stirred to react at 45° C. for 6 h to obtain *Poria cocos* etherification solution. For every 100 g of *Poria cocos* powder, 100 g of the chloroacetic acid solid was added.

Ethanol precipitation: 95% ethanol-acetic acid solution was added to the *Poria cocos* etherification solution for precipitation, and the precipitate was redissolved with water. Then ethanol solution with mass fraction of 95% was used for ethanol precipitation, and the precipitate was collected. The volume ratio of 95% ethanol-acetic acid solution to *Poria cocos* etherification solution was 3:1, and the 95% ethanol-acetic acid solution was prepared by mixing ethanol solution with mass fraction of 95% and acetic acid with mass fraction of 95% in 1:1 volume ratio.

Drying: the precipitate obtained in the ethanol precipitation step was dried by means of vacuum drying at 35° C. for 4 h to obtain the *Poria cocos* polysaccharide extract.

(2) *Atractylodes macrocephala* decoction pieces were crushed with a common Chinese herbal medicine pulverizer and sieved through 100 meshes to obtain *Atractylodes macrocephala* powder.

Ethanol extraction: ethanol solution was added into the *Atractylodes macrocephala* powder, subjected to heating and refluxing at 80° C. for 2 h, and was filtered to obtain *Atractylodes macrocephala* granules. The mass fraction of the ethanol solution was 75%, and the dosage was calculated by adding 20 mL ethanol solution per gram of *Atractylodes macrocephala* powder.

Ultrasonic extraction: distilled water was added to the *Atractylodes macrocephala* granules and extracted by ultrasonic at 75° C. for 60 min to obtain a filtrate, and the filtrate was filtered for standby.

Drying: vacuum freeze-drying was adopted, and the filtrate was prefrozen at −30° C. for 6 h before freeze-drying (the freeze-drying conditions were vacuum degree 10 Pa and cold trap temperature −55° C., and a setting procedure of diaphragm temperature was heating for 2 h at 10° C., heating for 3 h at 20° C., heating at 30° C., and freeze-drying for 20 h.) to obtain the *Atractylodes macrocephala* polysaccharide extract.

(3) *Radix codonopsis* decoction pieces were crushed with a common Chinese herbal medicine pulverizer and sieved through 100 meshes to obtain *Radix codonopsis* powder.

Microwave extraction: after soaking with water for 8 h, the *Radix codonopsis* powder was subjected to heating reaction in a microwave reactor at 250° C. for 1 h, and was filtered to obtain *Radix codonopsis* microwave extraction solution. 1000 mL purified water was added into every 100 g of *Radix codonopsis* powder.

Ethanol precipitation: 3 times volume of ethanol was added into the *Radix codonopsis* microwave extraction solution for ethanol precipitation, and after standing for 6 h and centrifuging for 10 min at 4000 r/min, the supernatant was removed, sewage reagent was added, swirled and mixed evenly, and then centrifuging was performed again for 10 min at 5000 r/min. The supernatant obtained by centrifugation was subjected to secondary ethanol precipitation and precipitate collection. The sewage reagent was prepared from trichloromethane and n-butanol according to a volume ratio of 4:1.

Drying: the precipitate obtained in the ethanol precipitation step was dried by means of vacuum drying at 35° C. for 4 h to obtain the *Radix codonopsis* polysaccharide extract. The steps (1), (2) and (3) are in no order.

(4) The *Poria cocos* polysaccharide extract, *Atractylodes macrocephala* polysaccharide extract and *Radix codonopsis* polysaccharide extract were mixed in the purified water and sterilized with high pressure steam at 121° C. for 30 min to obtain solution A.

L-tyrosine, α-cyclodextrin and polyethyleneimine were mixed in purified water and sterilized with high pressure steam at 121° C. for 30 min to obtain solution B. The steps (4) and (5) are in no order.

(5) Under aseptic operation environment, the solution A and solution B were mixed to obtain the freezing-drying protective agent.

The above *Poria cocos* decoction pieces, *Atractylodes macrocephala* decoction pieces and *Radix codonopsis* decoction pieces were purchased from China (Bozhou) Traditional Chinese Medicine Trading Center. L-tyrosine, α-cyclodextrin and polyethyleneimine are AR grade and purchased from Sinopharm Chemical Reagent Co., Ltd., Shanghai.

A direct-to-vat starter for aquatic fermentation feed included the above freeze-drying protective agent, *Enterococcus faecalis*, *Candida utilis*, *Aspergillus niger*, *Bacillus coagulans* and *Brevibacillus laterosporus*.

*Enterococcus faecalis*, CGMCC 1.15424, was purchased from China General Microbiological Culture Collection Center (CGMCC).

*Candida utilis*, CGMCC 2.3047, was purchased from China General Microbiological Culture Collection Center (CGMCC).

*Aspergillus niger*, CGMCC 3.15663, was purchased from China General Microbiological Culture Collection Center (CGMCC).

*Bacillus coagulans*, CGMCC 1.10823, purchased from China General Microbiological Culture Collection Center (CGMCC).

*Brevibacillus laterosporus*, CGMCC 1.15160, was purchased from China General Microbiological Culture Collection Center (CGMCC).

The preparation method of the above direct-to-vat starter for aquatic fermentation feed included the following steps.

(1) Strain activation: the slants of all strains were inoculated with the primary seed medium, and the primary seed solution was obtained after culture, and the seed solution was further activated and expanded for culture to obtain the secondary seed solution.

The activating conditions of *Enterococcus faecalis* strain were as follows. The primary seed culture conditions were 32° C., 48 hours. The inoculation amount of secondary was is 0.5%, the culture condition was 32° C., the shaking table culture was 120 r/min for 18 hours, and the seeds were stored at 4° C. for standby.

The activating conditions of *Candida utilis* strain were as follows. The primary seed culture conditions were 25° C., 48 hours. The inoculation amount of secondary seeds was 3.0%, the culture condition was 25° C., the shaking table culture was 120 r/min for 18 hours, and the seeds were stored at 4° C. for standby.

The activating conditions of *Aspergillus niger* strain were as follows. The primary seed culture conditions were 30° C., 20 hours. The inoculation amount of secondary seeds was 3.0%, the culture condition was 32° C., the shaking table culture was 120 r/min for 12 hours, and the seeds were stored at 4° C. for standby.

The activating conditions of *Bacillus coagulans* strain were as follows. The primary seed culture conditions were 45° C., 16 hours. The inoculation amount of secondary seeds was 1.0%, the culture condition was 45° C., the shaking table culture was 120 r/min for 12 hours, and the seeds were stored at 4° C. for standby.

The activating conditions of *Brevibacillus laterosporus* strain were as follows. The primary seed culture conditions were 20° C., 24 hours. The inoculation amount of secondary seeds was 2.0%, the culture condition was 20° C., the shaking table culture was 120 r/min for 28 hours, and the seeds were stored at 4° C. for standby.

The composition of primary and secondary seed culture media of *Enterococcus faecalis, Candida utilis, Aspergillus niger, Bacillus coagulans* and *Brevibacillus laterosporus* was as follows. Every 100 mL of the media contains 1.0 g of yeast powder, 2.0 g of beef extract, 2.5 g of tryptone, 0.1 g of sodium bicarbonate, 1.8 g of glucose, 0.1 g of sodium chloride, 0.1 g of sodium acetate, 0.015 g of magnesium sulfate and 0.005 g of manganese sulfate.

(2) After all strains were activated twice, they were inoculated into the multiplication medium. The inoculations of *Enterococcus faecalis, Candida utilis, Aspergillus niger, Bacillus coagulans* and *Brevibacillus laterosporus* were 2%, 1%, 2%, 3% and 2% respectively. Then mixed culture was carried out at 34° C. for 12 h, centrifugation was carried out after culture and the supernatant was discarded. The same amount of sterilized 0.85% physiological saline was added to wash the cells twice. Under the same conditions, the mixed sludge of *Enterococcus faecalis, Candida utilis, Aspergillus niger, Bacillus coagulans* and *Brevibacillus laterosporus* was obtained by centrifugation. The mixed sludge was suspended in physiological saline, and the final volume was 1/10 of the original fermentation liquid volume to prepare the mixed strain solution. The viable concentration in the mixed strain solution was determined to meet the following range:

the viable concentration of *Enterococcus faecalis* was $1.0 \times 10^{10} \sim 6.0 \times 10^{10}$ CFU/mL;

the viable concentration of *Candida utilis* was $3.0 \times 10^{8} \sim 6.0 \times 10^{8}$ CFU/mL;

the viable concentration of *Aspergillus niger* was $8.0 \times 10^{7} \sim 2.0 \times 10^{8}$ CFU/mL;

the viable concentration of *Bacillus coagulans* was $5.0 \times 10^{7} \sim 3.0 \times 10^{8}$ CFU/mL; and the viable concentration of *Brevibacillus laterosporus* was $1.0 \times 10^{8} \sim 4.0 \times 10^{8}$ CFU/mL.

The freeze-drying protective agent was added into the mixed strain solution to obtain the mixed solution. The volume ratio of mixed strain solution and freeze-drying protective agent was 1:1.

The multiplication medium was composite medium of Jerusalem artichoke and *Poria cocos*.

The preparation method of the composite culture medium of Jerusalem artichoke and *Poria cocos* included: mixing Jerusalem artichoke powder, *Poria cocos* water extract and water at a ratio of 2:3:5 (w/w/w), hydrolyzing at 65° C. for 60 min, heating to 95° C. and hydrolyzing for 60 min, cooling, filtering with 8 layers of gauze, and adjusting pH value of the filtrate to 7.0~7.3 to obtain the composite culture medium of Jerusalem artichoke and *Poria cocos;*

The preparation method of the Jerusalem artichoke powder included: slicing fresh Jerusalem artichoke, drying the fresh Jerusalem artichoke slices at 70° C. until the water content is lower than 8%, and then crushing the dried Jerusalem artichoke slices and sieving the crushed Jerusalem artichoke slices through 100 meshes to obtain the Jerusalem artichoke powder.

The preparation method of the *Poria cocos* water extract included: slicing fresh *Poria cocos*, drying the fresh *Poria cocos* slices at 70° C., and then crushing the dried *Poria cocos* slices; adding 10 times the mass of absolute ethanol, extracting for 2 h and subjecting the extract to filtering to obtain a residue; adding 8 times the mass of distilled water to the residue, heating and refluxing to extract for 2 h, filtering twice to obtain filtrates, combining the filtrates, subjecting the combined filtrate to concentrating and drying under reduced pressure to obtain the *Poria cocos* water extract.

(3) Freeze-drying: 2 mL of mixed solution obtained in step (2) was taken and put into vials. The prefreezing process was carried out for 3 h at −80° C., and the strain solution was quickly transferred to a vacuum freeze-drying machine for freeze-drying after being completely frozen. The freeze-drying conditions are vacuum degree 10 Pa and cold trap temperature −55° C. And a setting procedure of diaphragm temperature is heating for 2 h at 10° C., heating for 3 h at 20° C., heating at 30° C., and freeze-drying for 20 h.

The starter was obtained after freeze-drying, the finished product was obtained after aseptic packaging, and was stored at 4° C.

The performance of direct-to-vat starter was evaluated by freeze-drying survival rate and fermentation activity.

The freeze-drying survival rate was calculated by rehydrating the freeze-dried cell powder to the volume before freeze-drying, and culturing and counting it in the appropriate medium of *Enterococcus faecalis, Candida utilis, Aspergillus niger, Bacillus coagulans* and *Brevibacillus laterosporus*. Cell survival rate=total viable cells measured after freeze-drying/total viable cells measured before freeze-drying×100%.

TABLE 1

| | Viable count and survival rate of direct-to-vat starter in each storage period | | | | | | | | |
|---|---|---|---|---|---|---|---|---|---|
| | Storage time (d) | | | | | | | | |
| Evaluating indicator | 0 | 15 | 30 | 45 | 60 | 75 | 90 | 120 | 150 |
| Viable count (CFU/g) | $5.6 \times 10^{10}$ | $5.4 \times 10^{10}$ | $5.6 \times 10^{10}$ | $5.5 \times 10^{10}$ | $5.3 \times 10^{10}$ | $5.4 \times 10^{10}$ | $5.4 \times 10^{10}$ | $5.5 \times 10^{10}$ | $5.5 \times 10^{10}$ |
| survival rate (%) | 96.6 | 93.1 | 96.6 | 94.8 | 91.4 | 93.1 | 93.1 | 94.8 | 94.8 |

After 150 days of storage at 4° C., the viable count in the direct-to-vat starter made of *Poria cocos, Atractylodes macrocephala, Radix codonopsis* compound polysaccharide extracts remained above $10^{10}$ CFU/g, the survival rate was still 94.8%, and the survival rate was stable at 91.4~96.6% during the whole storage process.

The evaluation method of fermentation activity was to use 1.5% inoculum of the direct-to-vat starter stored for 150 days into 10% Jerusalem artichoke juice for fermentation, and evaluate the changes of viable count, pH value, reducing sugar, total sugar and total amino nitrogen during the fermentation process of the starter. Inoculation of direct activated expanded culture seed solution of strain was as the control.

TABLE 2

Evaluation of fermentation performance of direct-to-vat starter after 150 days of storage

| | Fermentation process (h) | | | | | |
| | 0 | | 6 | | 12 | |
| Evaluating indicator | Direct-to-vat | Control | Direct-to-vat | Control | Direct-to-vat | Control |
|---|---|---|---|---|---|---|
| Viable count (CFU/mL) | $1.1 \times 10^8$ | $1.0 \times 10^8$ | $7.5 \times 10^8$ | $7.5 \times 10^8$ | $1.2 \times 10^{10}$ | $1.3 \times 10^{10}$ |
| pH value | 6.3 | 6.3 | 5.5 | 5.7 | 5.2 | 5.0 |
| Reducing sugar (mg/mL) | 5.4 | 5.4 | 3.9 | 3.3 | 1.6 | 1.4 |
| Total sugar (mg/mL) | 57.9 | 58.1 | 56.5 | 55.9 | 52.3 | 51.8 |
| Total amino nitrogen (mg/mL) | 0.85 | 0.84 | 0.81 | 0.80 | 0.74 | 0.75 |

| | Fermentation process (h) | | | | | |
| | 18 | | 24 | | 30 | |
| Evaluating indicator | Direct-to-vat | Control | Direct-to-vat | Control | Direct-to-vat | Control |
|---|---|---|---|---|---|---|
| Viable count (CFU/mL) | $1.01 \times 10^{10}$ | $1.1 \times 10^{10}$ | $8.5 \times 10^9$ | $8.6 \times 10^9$ | $6.2 \times 10^8$ | $6.3 \times 10^8$ |
| pH value | 4.2 | 4.1 | 3.7 | 3.6 | 3.8 | 3.8 |
| Reducing sugar (mg/mL) | 1.3 | 1.3 | 1.2 | 1.1 | 1.1 | 1.1 |
| Total sugar (mg/mL) | 49.5 | 48.7 | 48.2 | 47.5 | 47.9 | 47.4 |
| Total amino nitrogen (mg/mL) | 0.68 | 0.68 | 0.71 | 0.69 | 0.66 | 0.65 |

The direct-to-vat starter made of *Poria cocos, Atractylodes macrocephala* and *Radix codonopsis* compound polysaccharide extract freeze-drying protective agent can maintain high fermentation activity. In the process of fermentation of 10% Jerusalem artichoke juice, the cells grew rapidly, had strong acid production capacity, and consumed reducing sugar and total sugar quickly, and the overall effect was not significantly different from that of direct activation inoculation.

The viable count in Table 1 and Table 2 was the sum of the viable count of *Enterococcus faecalis, Candida utilis, Aspergillus niger, Bacillus coagulans* and *Brevibacillus laterosporus*.

Embodiment 2

A freeze-drying protective agent included the following components: *Poria cocos* polysaccharide extract 30.0 g/100 mL, *Atractylodes macrocephala* polysaccharide extract 20.0 g/100 mL, *Radix codonopsis* polysaccharide extract 20.0 g/100 mL, L-tyrosine 10.0 g/100 mL, α-cyclodextrin 7.0 g/100 mL and polyethyleneimine 5.0 g/100 mL.

The preparation method of the freeze-drying protective agent included the following steps.

(1) *Poria cocos* decoction pieces were crushed with a common Chinese herbal medicine pulverizer and sieved through 100 meshes to obtain *Poria cocos* powder.

Alkalization: NaOH solution was added to the *Poria cocos* powder and continuously stirred until the *Poria cocos* powder was completely dissolved to obtain *Poria cocos* alkalization solution. 300 mL of NaOH solution was added to every 100 g of *Poria cocos* powder, and the mass fraction of NaOH solution was 50%.

Etherification: chloroacetic acid solid (domestic analytical pure) was slowly added to the *Poria cocos* alkalization solution in batches and continuously stirred to react at 50° C. for 7 h to obtain *Poria cocos* etherification solution. For every 100 g of *Poria cocos* powder, 50 g of the chloroacetic acid solid was added.

Ethanol precipitation: 95% ethanol-acetic acid solution was added to the *Poria cocos* etherification solution for precipitation, and the precipitate was redissolved with water. Then ethanol solution with mass fraction of 95% was used for ethanol precipitation, and the precipitate was collected. The volume ratio of 95% ethanol-acetic acid solution to *Poria cocos* etherification solution was 4:1, and the 95% ethanol-acetic acid solution was prepared by mixing ethanol solution with mass fraction of 95% and acetic acid with mass fraction of 95% in 1:1 volume ratio.

Drying: the precipitate obtained in the ethanol precipitation step was dried by means of vacuum drying at 40° C. for 5 h to obtain the *Poria cocos* polysaccharide extract.

(2) *Atractylodes macrocephala* decoction pieces were crushed with a common Chinese herbal medicine pulverizer and sieved through 100 meshes to obtain *Atractylodes macrocephala* powder.

Ethanol extraction: ethanol solution was added into the *Atractylodes macrocephala* powder, subjected to heating and refluxing at 82° C. for 2 h, and was filtered to obtain *Atractylodes macrocephala* granules. The mass fraction of the ethanol solution was 75%, and the dosage was calculated by adding 20 mL ethanol solution per gram of *Atractylodes macrocephala* powder.

Ultrasonic extraction: distilled water was added to the *Atractylodes macrocephala* granules and extracted by ultrasonic at 80° C. for 80 min to obtain a filtrate, and the filtrate was filtered for standby.

Drying: vacuum freeze-drying was adopted, and the filtrate was prefrozen at −30° C. for 6 h before freeze-drying (the freeze-drying conditions were vacuum degree 10 Pa and cold trap temperature −55° C., and a setting procedure of diaphragm temperature was heating for 2 h at 10° C., heating for 3 h at 20° C., heating at 30° C., and freeze-drying for 20 h.) to obtain the *Atractylodes macrocephala* polysaccharide extract.

(3) *Radix codonopsis* decoction pieces were crushed with a common Chinese herbal medicine pulverizer and sieved through 100 meshes to obtain *Radix codonopsis* powder.

Microwave extraction: after soaking with water for 10 h, the *Radix codonopsis* powder was subjected to heating reaction in a microwave reactor at 250° C. for 1 h, and was filtered to obtain *Radix codonopsis* microwave extraction solution. 1500 mL purified water was added into every 100 g of *Radix codonopsis* powder.

Ethanol precipitation: 4 times volume of ethanol was added into the *Radix codonopsis* microwave extraction solution for ethanol precipitation, and after standing for 7 h and centrifuging for 12 min at 4000 r/min, the supernatant was removed, sewage reagent was added, swirled and mixed evenly, and then centrifuging was performed again for 12 min at 5000 r/min. The supernatant obtained by centrifugation was subjected to secondary ethanol precipitation and precipitate collection. The sewage reagent was prepared from trichloromethane and n-butanol according to a volume ratio of 4:1.

Drying: the precipitate obtained in the ethanol precipitation step was dried by means of vacuum drying at 40° C. for 5 h to obtain the *Radix codonopsis* polysaccharide extract.

The steps (1), (2) and (3) are in no order.

(4) The *Poria cocos* polysaccharide extract, *Atractylodes macrocephala* polysaccharide extract and *Radix codonopsis* polysaccharide extract were mixed in the purified water and sterilized with high pressure steam at 121° C. for 30 min to obtain solution A.

L-tyrosine, α-cyclodextrin and polyethyleneimine were mixed in purified water and sterilized with high pressure steam at 121° C. for 30 min to obtain solution B.

The steps (4) and (5) are in no order.

(5) Under aseptic operation environment, the solution A and solution B were mixed to obtain the freezing-drying protective agent.

The above *Poria cocos* decoction pieces, *Atractylodes macrocephala* decoction pieces and *Radix codonopsis* decoction pieces were purchased from China (Bozhou) Traditional Chinese Medicine Trading Center. L-tyrosine, α-cyclodextrin and polyethyleneimine are AR grade and purchased from Sinopharm Chemical Reagent Co., Ltd., Shanghai.

A direct-to-vat starter for aquatic fermentation feed included the above freeze-drying protective agent, *Enterococcus faecalis, Candida utilis, Aspergillus niger, Bacillus coagulans* and *Brevibacillus laterosporus.*

*Enterococcus faecalis*, CGMCC 1.15424, was purchased from China General Microbiological Culture Collection Center (CGMCC).

*Candida utilis*, CGMCC 2.3047, was purchased from China General Microbiological Culture Collection Center (CGMCC).

*Aspergillus niger*, CGMCC 3.15663, was purchased from China General Microbiological Culture Collection Center (CGMCC).

*Bacillus coagulans*, CGMCC 1.10823, purchased from China General Microbiological Culture Collection Center (CGMCC).

*Brevibacillus laterosporus*, CGMCC 1.15160, was purchased from China General Microbiological Culture Collection Center (CGMCC).

The preparation method of the above direct-to-vat starter for aquatic fermentation included the following steps.

(1) Strain activation: the slants of all strains were inoculated with the primary seed medium, and the primary seed solution was obtained after culture, and the seed solution was further activated and expanded for culture to obtain the secondary seed solution.

The activating conditions of *Enterococcus faecalis* strain were as follows. The primary seed culture conditions were 34° C., 48 hours. The inoculation amount of secondary was is 1.0%, the culture condition was 34° C., the shaking table culture was 150 r/min for 18 hours, and the seeds were stored at 4° C. for standby.

The activating conditions of *Candida utilis* strain were as follows. The primary seed culture conditions were 26° C., 48 hours. The inoculation amount of secondary seeds was 4.6%, the culture condition was 26° C., the shaking table culture was 150 r/min for 18 hours, and the seeds were stored at 4° C. for standby.

The activating conditions of *Aspergillus niger* strain were as follows. The primary seed culture conditions were 32° C., 20 hours. The inoculation amount of secondary seeds was 5.0%, the culture condition was 32° C., the shaking table culture was 150 r/min for 18 hours, and the seeds were stored at 4° C. for standby.

The activating conditions of *Bacillus coagulans* strain were as follows. The primary seed culture conditions were 45° C., 16 hours. The inoculation amount of secondary seeds was 2.0%, the culture condition was 45° C., the shaking table culture was 120 r/min for 12 hours, and the seeds were stored at 4° C. for standby.

The activating conditions of *Brevibacillus laterosporus* strain were as follows. The primary seed culture conditions were 30° C., 24 hours. The inoculation amount of secondary seeds was 4.0%, the culture condition was 30° C., the shaking table culture was 150 r/min for 30 hours, and the seeds were stored at 4° C. for standby.

The composition of primary and secondary seed culture media of *Enterococcus faecalis, Candida utilis, Aspergillus niger, Bacillus coagulans* and *Brevibacillus laterosporus* was as follows. Every 100 mL of the media contains 1.8 g of yeast powder, 2.4 g of beef extract, 3.0 g of tryptone, 0.1 g of sodium bicarbonate, 2.4 g of glucose, 0.2 g of sodium chloride, 0.1 g of sodium acetate, 0.015 g of magnesium sulfate and 0.006 g of manganese sulfate.

(2) After all strains were activated twice, they were inoculated into the multiplication medium. The inoculations of *Enterococcus faecalis, Candida utilis, Aspergillus niger, Bacillus coagulans* and *Brevibacillus laterosporus* were 3%, 2%, 3%, 4%, and 3% respectively. Then mixed culture was carried out at 34° C. for 12 h, centrifugation was carried out after culture and the supernatant was discarded. The same amount of sterilized 0.85% physiological saline was added to wash the cells twice. Under the same conditions, the mixed sludge of *Enterococcus faecalis, Candida utilis, Aspergillus niger, Bacillus coagulans* and *Brevibacillus laterosporus* was obtained by centrifugation. The mixed sludge was suspended in physiological saline, and the final volume was 1/10 of the original fermentation liquid volume to prepare the mixed strain solution. The viable concentration in the mixed strain solution was determined to meet the following range:

the viable concentration of *Enterococcus faecalis* was $1.0\times10^{10}$~$6.0\times10^{10}$ CFU/mL;

the viable concentration of *Candida utilis* was $3.0\times10^8$~$6.0\times10^8$ CFU/mL;

the viable concentration of *Aspergillus niger* was $8.0\times10^7$~$2.0\times10^8$ CFU/mL;

the viable concentration of *Bacillus coagulans* was $5.0\times10^7$~$3.0\times10^8$ CFU/mL; and the viable concentration of *Brevibacillus laterosporus* was $1.0\times10^8$~$4.0\times10^8$ CFU/mL.

The freeze-drying protective agent was added into the mixed strain solution to obtain the mixed solution. The volume ratio of mixed strain solution and freeze-drying protective agent was 1:3.

The multiplication medium was composite medium of Jerusalem artichoke and *Poria cocos*.

The preparation method of the composite culture medium of Jerusalem artichoke and *Poria cocos* included: mixing Jerusalem artichoke powder, *Poria cocos* water extract and water at a ratio of 2:3:5 (w/w/w), hydrolyzing at 65° C. for 60 min, heating to 95° C. and hydrolyzing for 60 min, cooling, filtering with 8 layers of gauze, and adjusting pH value of the filtrate to 7.0~7.3 to obtain the composite culture medium of Jerusalem artichoke and *Poria cocos;*

The preparation method of the Jerusalem artichoke powder included: slicing fresh Jerusalem artichoke, drying the fresh Jerusalem artichoke slices at 75° C. until the water content is lower than 8%, and then crushing the dried Jerusalem artichoke slices and sieving the crushed Jerusalem artichoke slices through 100 meshes to obtain the Jerusalem artichoke powder.

The preparation method of the *Poria cocos* water extract included: slicing fresh *Poria cocos*, drying the fresh *Poria cocos* slices at 75° C., and then crushing the dried *Poria cocos* slices; adding 12 times the mass of absolute ethanol, extracting for 3 h and subjecting the extract to filtering to obtain a residue; adding 10 times the mass of distilled water to the residue, heating and refluxing to extract for 2 h, filtering twice to obtain filtrates, combining the filtrates, subjecting the combined filtrate to concentrating and drying under reduced pressure to obtain the *Poria cocos* water extract.

(3) Freeze-drying: 2 mL of mixed solution obtained in step (2) was taken and put into vials. The prefreezing process was carried out for 3 h at −80° C., and the strain solution was quickly transferred to a vacuum freeze-drying machine for freeze-drying after being completely frozen. The freeze-drying conditions are vacuum degree 10 Pa and cold trap temperature −55° C. And a setting procedure of diaphragm temperature is heating for 2 h at 10° C., heating for 3 h at 20° C., heating at 30° C., and freeze-drying for 20 h.

The starter was obtained after freeze-drying, the finished product was obtained after aseptic packaging, and was stored at 4° C.

The freeze-drying survival rate and fermentation activity of the direct-to-vat starter were evaluated.

TABLE 3

Viable count and survival rate of direct-to-vat starter in each storage period

| | Storage time (d) | | | | | | | | |
|---|---|---|---|---|---|---|---|---|---|
| Evaluating indicator | 0 | 15 | 30 | 45 | 60 | 75 | 90 | 120 | 150 |
| Viable count (CFU/g) | $6.2 \times 10^{10}$ | $6.1 \times 10^{10}$ | $6.1 \times 10^{10}$ | $6.0 \times 10^{10}$ | $6.2 \times 10^{10}$ | $6.1 \times 10^{10}$ | $6.1 \times 10^{10}$ | $6.2 \times 10^{10}$ | $6.1 \times 10^{10}$ |
| survival rate (%) | 96.9 | 95.3 | 95.3 | 93.8 | 96.9 | 95.3 | 95.3 | 96.9 | 95.3 |

After 150 days of storage at 4° C., the viable count in the direct-to-vat starter made of *Poria cocos, Atractylodes macrocephala, Radix codonopsis* compound polysaccharide extract freeze-drying protective agent remained above $10^{10}$ CFU/g, the survival rate was still 95.3%, and the survival rate was stable at 93.8~96.9% during the whole storage process.

1.5% inoculum of the direct-to-vat starter stored for 150 days into 10% Jerusalem artichoke juice for fermentation was used, and the changes of viable count, pH value, reducing sugar, total sugar and total amino nitrogen during the fermentation process of the starter were evaluated. Inoculation of direct activated expanded culture seed solution of strain was as the control.

TABLE 4

Evaluation of fermentation performance of direct-to-vat starter after 150 days of storage

| | Fermentation process (h) | | | | | |
|---|---|---|---|---|---|---|
| | 0 | | 6 | | 12 | |
| Evaluating indicator | Direct-to-vat | Control | Direct-to-vat | Control | Direct-to-vat | Control |
| Viable count (CFU/mL) | $1.3 \times 10^8$ | $1.3 \times 10^8$ | $7.9 \times 10^8$ | $7.8 \times 10^8$ | $1.5 \times 10^{10}$ | $1.5 \times 10^{10}$ |
| pH value | 6.3 | 6.3 | 5.4 | 5.3 | 5.3 | 5.2 |
| Reducing sugar (mg/mL) | 5.3 | 5.3 | 3.5 | 3.2 | 1.7 | 1.6 |
| Total sugar (mg/mL) | 56.4 | 56.2 | 55.2 | 55.0 | 51.2 | 51.1 |
| Total amino nitrogen (mg/mL) | 0.86 | 0.84 | 0.80 | 0.79 | 0.73 | 0.74 |

| | Fermentation process (h) | | | | | |
|---|---|---|---|---|---|---|
| | 18 | | 24 | | 30 | |
| Evaluating indicator | Direct-to-vat | Control | Direct-to-vat | Control | Direct-to-vat | Control |
| Viable count (CFU/mL) | $1.5 \times 10^{10}$ | $1.5 \times 10^{10}$ | $7.9 \times 10^9$ | $8.2 \times 10^9$ | $9.5 \times 10^8$ | $9.4 \times 10^8$ |
| pH value | 4.3 | 4.1 | 3.8 | 3.7 | 3.7 | 3.6 |

TABLE 4-continued

| Evaluation of fermentation performance of direct-to-vat starter after 150 days of storage | | | | | | |
|---|---|---|---|---|---|---|
| Reducing sugar (mg/mL) | 1.1 | 1.0 | 1.0 | 1.1 | 1.0 | 1.0 |
| Total sugar (mg/mL) | 47.5 | 47.7 | 45.3 | 45.8 | 44.9 | 44.8 |
| Total amino nitrogen (mg/mL) | 0.67 | 0.68 | 0.68 | 0.68 | 0.67 | 0.66 |

The direct-to-vat starter made of *Poria cocos, Atractylodes macrocephala* and *Radix codonopsis* compound polysaccharide extract freeze-drying protective agent can maintain high fermentation activity. In the process of fermentation of 10% Jerusalem artichoke juice, the cells grew rapidly, had strong acid production capacity, and consumed reducing sugar and total sugar quickly, and the overall effect was not significantly different from that of direct activation inoculation.

The viable count in Table 3 and Table 4 was the sum of the viable count of *Enterococcus faecalis, Candida utilis, Aspergillus niger, Bacillus coagulans* and *Brevibacillus laterosporus.*

Embodiment 3

The freeze-drying protective agent was prepared according to the components shown in Table 5, and the direct-to-vat starter was prepared. The specific steps and parameter settings of the experimental process were carried out according to embodiment 2.

TABLE 5

| Experimental design | |
|---|---|
| Experimental group | Components |
| Experiment 1 | *Poria cocos* polysaccharide extract 20.0 g/100 mL, L-tyrosine 5.0 g/100 mL, α-cyclodextrin 5.0 g/100 mL, polyethyleneimine 3.0 g/100 mL |
| Experiment 2 | *Atractylodes macrocephala* polysaccharide extract 15.0 g/100 mL, L-tyrosine 5.0 g/100 mL, α-cyclodextrin 5.0 g/100 mL, polyethyleneimine 3.0 g/100 mL |
| Experiment 3 | *Radix Codonopsis* polysaccharide extract 12.0 g/100 mL, L-tyrosine 5.0 g/100 mL, α-cyclodextrin 5.0 g/100 mL, polyethyleneimine 3.0 g/100 mL |
| Experiment 4 | *Poria cocos* polysaccharide extract 20.0 g/100 mL, *Atractylodes macrocephala* polysaccharide extract 15.0 g/100 mL, L-tyrosine 5.0 g/100 mL, α-cyclodextrin 5.0 g/100 mL, polyethyleneimine 3.0 g/100 mL |

TABLE 5-continued

| Experimental design | |
|---|---|
| Experimental group | Components |
| Experiment 5 | *Poria cocos* polysaccharide extract 20.0 g/100 mL, *Radix Codonopsis* polysaccharide extract 12.0 g/100 mL, L-tyrosine 5.0 g/100 mL, α-cyclodextrin 5.0 g/ 100 mL, polyethyleneimine 3.0 g/100 mL |
| Experiment 6 | *Atractylodes macrocephala* polysaccharide extract 15.0 g/100 mL, *Radix Codonopsis* polysaccharide extract 12.0 g/100 mL, L-tyrosine 5.0 g/100 mL, α-cyclodextrin 5.0 g/100 mL, polyethyleneimine 3.0 g/100 mL |
| Experiment 7 | *Poria cocos* polysaccharide extract 20.0 g/100 mL, *Atractylodes macrocephala* polysaccharide extract 15.0 g/100 mL, *Radix Codonopsis* polysaccharide extract 12.0 g/100 mL, L-tyrosine 5.0 g/100 mL, α-cyclodextrin 5.0 g/100 mL, polyethyleneimine 3.0 g/100 mL |

The freeze-drying survival rates of cells after different storage time were shown in Table 6.

TABLE 6

| Freeze-drying survival rate in different groups during storage (%) | | | | | | | | | |
|---|---|---|---|---|---|---|---|---|---|
| | Storage time (d) | | | | | | | | |
| Experimental group | 0 | 15 | 30 | 45 | 60 | 75 | 90 | 120 | 150 |
| Experiment 1 | 32.1 | 30.0 | 23.6 | 11.2 | 10.2 | 9.8 | 7.5 | 7.2 | 6.2 |
| Experiment 2 | 26.7 | 25.4 | 22.2 | 18.3 | 7.6 | 6.1 | 5.7 | 5.6 | 4.5 |
| Experiment 3 | 27.5 | 18.9 | 16.2 | 10.1 | 8.7 | 6.2 | 5.6 | 4.1 | 3.9 |
| Experiment 4 | 62.1 | 48.9 | 45.1 | 40.8 | 38.7 | 34.6 | 32.3 | 30.1 | 29.9 |
| Experiment 5 | 58.1 | 40.1 | 40.2 | 39.4 | 35.1 | 36.0 | 28.7 | 27.3 | 22.1 |
| Experiment 6 | 64.5 | 49.2 | 39.7 | 32.8 | 29.4 | 16.7 | 11.2 | 9.5 | 6.3 |
| Experiment 7 | 96.9 | 95.0 | 95.2 | 94.3 | 95.2 | 93.2 | 94.3 | 95.1 | 94.4 |

It can be seen from Table 5 and Table 6 that the freeze-drying survival rate of cells can be significantly improved by using the polysaccharide extract freeze-drying protective agent in experiment 7. Especially during the 150-day storage period, the protective agent in experiment 7 had a significant effect compared with the use alone or paired.

Embodiment 4

The freeze-drying protective agent and direct-to-vat starter were prepared according to the experiment 7 of embodiment 3. The specific steps and parameter settings of the experimental process were carried out according to embodiment 2. The mixing ratio (v/v) of mixed strain solution and freeze-drying protective agent was adjusted.

TABLE 7

Freeze-drying survival rate during storage under different mixing ratio (%)

| Different mixing ratio | Storage time (d) | | | | | | | | |
|---|---|---|---|---|---|---|---|---|---|
| | 0 | 15 | 30 | 45 | 60 | 75 | 90 | 120 | 150 |
| 1:0.5 | 83.1 | 82.8 | 81.1 | 75.4 | 73.2 | 72.1 | 70.0 | 64.5 | 69.9 |
| 1:1.0 | 90.1 | 90.5 | 90.1 | 89.1 | 89.1 | 85.4 | 88.4 | 86.5 | 87.9 |
| 1:1.5 | 91.1 | 88.7 | 89.7 | 90.1 | 90.5 | 90.0 | 85.6 | 88.7 | 90.0 |
| 1:2.0 | 92.1 | 91.5 | 91.7 | 91.2 | 90.5 | 90.1 | 89.8 | 90.0 | 90.1 |
| 1:2.5 | 95.0 | 94.5 | 95.1 | 91.2 | 92.5 | 92.7 | 91.9 | 91.5 | 92.0 |
| 1:3.0 | 96.9 | 95.0 | 95.2 | 94.3 | 95.2 | 93.2 | 94.3 | 95.1 | 94.4 |
| 1:3.5 | 95.8 | 94.8 | 95.3 | 94.7 | 95.1 | 94.0 | 94.2 | 95.2 | 94.5 |
| 1:4.0 | 97.1 | 95.1 | 95.2 | 94.9 | 95.1 | 94.4 | 94.5 | 95.1 | 94.4 |
| 1:4.5 | 94.2 | 94.0 | 94.2 | 92.5 | 90.1 | 87.2 | 85.1 | 80.2 | 79.5 |
| 1:5.0 | 9.6 | 93.2 | 92.1 | 91.0 | 90.0 | 89.2 | 87.1 | 82.3 | 80.1 |

It can be seen from the above table that when the volume ratio of mixed strain solution to freeze-drying protective agent was 1:1~1:4, the freeze-drying survival rate of cells can still reach 87.9~94.5% on the 150th day of storage. When the volume ratio was 1:0.5, the freeze-drying survival rate decreased significantly, and at the 150th day of storage, the freeze-drying survival rate was only 69.9%. When the volume ratio was 1:4.5 and 1:5.0, the freeze-drying survival rates were 79.5% and 80.1%, respectively. Therefore, the volume ratio of the concentrated strain cell suspension and fermentation performance was as described in embodiment 2.

The results were as shown in Table 8. Compared with the commercial direct-to-vat starter, the direct-to-vat starter of the present disclosure can maintain a higher fermentation activity. In the process of fermenting 10% Jerusalem artichoke juice, the direct-to-vat starter of the present disclosure had the fastest fermentation speed, the cells grew rapidly and had the best acid production performance.

TABLE 8

Comparison of fermentation performance between the direct-to-vat starter of the present disclosure and the commercial starters

| Sample | Fermentation process (h) | | | | | |
|---|---|---|---|---|---|---|
| | 0 | 6 | 12 | 18 | 24 | 30 |
| | Viable count (CFU/mL) | | | | | |
| Direct-to-vat starter of present disclosure | $2.3 \times 10^8$ | $7.9 \times 10^8$ | $3.5 \times 10^{10}$ | $2.0 \times 10^{10}$ | $8.8 \times 10^9$ | $3.1 \times 10^9$ |
| Commercial starter 1 | $5.2 \times 10^8$ | $6.0 \times 10^8$ | $7.6 \times 10^9$ | $9.1 \times 10^9$ | $9.5 \times 10^9$ | $1.0 \times 10^9$ |
| Commercial starter 2 | $7.1 \times 10^7$ | $8.0 \times 10^7$ | $1.0 \times 10^8$ | $6.0 \times 10^8$ | $2.2 \times 10^9$ | $1.9 \times 10^8$ |
| Commercial starter 3 | $3.5 \times 10^8$ | $1.6 \times 10^8$ | $2.7 \times 10^9$ | $1.9 \times 10^{10}$ | $3.2 \times 10^9$ | $1.2 \times 10^9$ |
| Commercial starter 4 | $9.0 \times 10^7$ | $1.0 \times 10^8$ | $2.1 \times 10^{10}$ | $9.1 \times 10^9$ | $3.7 \times 10^8$ | $1.5 \times 10^8$ |
| | pH value | | | | | |
| Direct-to-vat starter of present disclosure | 6.3 | 5.2 | 4.7 | 4.0 | 3.6 | 3.6 |
| Commercial starter 1 | 6.3 | 5.9 | 5.3 | 4.5 | 4.1 | 3.8 |
| Commercial starter 2 | 6.3 | 5.7 | 5.0 | 4.3 | 3.9 | 3.7 |
| Commercial starter 3 | 6.3 | 5.6 | 5.4 | 4.6 | 4.2 | 3.8 |
| Commercial starter 4 | 6.3 | 5.5 | 4.9 | 4.5 | 4.1 | 3.9 | the freeze-drying protective agent preferred by the disclosure was 1:1~1:4. Further, it was preferably 1:1.5 to 1:4. Further, it was preferably 1:2.5 to 1:4.

Embodiment 5

On the formula of experiment 7 in embodiment 3, the direct-to-vat starter was prepared according to the best ratio selected in embodiment 4. In addition, four kinds of commercial direct-to-vat starter (all within the shelf life) were purchased, and the differences in the Viable count and pH value on fermentation performance between the direct-to-vat starter and the commercial starter were dynamically compared and analyzed. The method for evaluation of Various embodiments in the present specification are described in a progressive manner, and the emphasizing description of each embodiment is different from the other embodiments. The same and similar parts of various embodiments can be referred to for each other.

The above description of the disclosed embodiments enables the skilled in the art to achieve or use the disclosure. Multiple modifications to these embodiments will be apparent to those skilled in the art, and the general principles defined herein may be achieved in other embodiments without departing from the spirit or scope of the disclosure. The present disclosure will therefore not be restricted to these embodiments shown herein, but rather to comply with the broadest scope consistent with the principles and novel features disclosed herein.

What is claimed is:

1. A preparation method of a direct-to-vat starter, comprising mixing a mixed strain solution of *Enterococcus faecalis, Candida utilis, Aspergillus niger, Bacillus coagulans* and *Brevibacillus laterosporus* with a freeze-drying protective agent according to a volume ratio of 1:1 to 1:4, and carrying out freeze-drying to obtain the direct-to-vat starter; wherein the freeze-drying protective agent consists of the following components:

*Poria cocos* polysaccharide extract 10.0-30.0 g/100 mL, *Atractylodes macrocephala* polysaccharide extract 10.0-20.0 g/100 mL, *Radix codonopsis* polysaccharide extract 5.0-20.0 g/100 mL, L-tyrosine 2.0-10.0 g/100 mL, α-cyclodextrin 2.0-7.0 g/100 mL and polyethyleneimine 2.0-5.0 g/100 mL.

2. The preparation method of claim 1, wherein in the mixed strain solution, the viable concentration of *Enterococcus faecalis* is $1.0 \times 10^{10}$-$6.0 \times 10^{10}$ CFU/mL;

the viable concentration of *Candida utilis* is $3.0 \times 10^8$-$6.0 \times 10^8$ CFU/mL;

the viable concentration of *Aspergillus niger* is $8.0 \times 10^7$-$2.0 \times 10^8$ CFU/mL;

the viable concentration of *Bacillus coagulans* is $5.0 \times 10^7$-$3.0 \times 10^8$ CFU/mL; and the viable concentration of *Brevibacillus laterosporus* is $1.0 \times 10^8$-$4.0 \times 10^8$ CFU/mL.

3. The preparation method of claim 2, wherein a preparation method of the mixed strain solution of *Enterococcus faecalis, Candida utilis, Aspergillus niger, Bacillus coagulans* and *Brevibacillus laterosporus* comprises:

(1) activating *Enterococcus faecalis, Candida utilis, Aspergillus niger, Bacillus coagulans* and *Brevibacillus laterosporus* respectively;

(2) after activation, mixing all activated strains and inoculating with a multiplication medium for multiplication culture, culturing the strains at 34° C. for 12 h, after culture is carried out, centrifuging the culture and discarding the supernatant, and performing resuspension with physiological saline to obtain the mixed strain solution;

the multiplication medium used in the process of multiplication culture is a composite medium of Jerusalem artichoke and *Poria cocos;* a preparation method of the composite medium of Jerusalem artichoke and *Poria cocos* comprises: mixing Jerusalem artichoke powder, *Poria cocos* water extract and water at a mass ratio of 2:3:5, hydrolyzing at 65° C. for 60 min, heating to 95° C. and hydrolyzing for 60 min, cooling, filtering with 8 layers of gauze, and adjusting pH value of the filtrate to 7.0~7.3 to obtain the composite medium of Jerusalem artichoke and *Poria cocos;* a preparation method of the Jerusalem artichoke powder comprises: slicing fresh Jerusalem artichoke, drying the fresh Jerusalem artichoke slices at 70~80° C. until the water content is lower than 8%, and then crushing the dried Jerusalem artichoke slices and sieving the crushed Jerusalem artichoke slices through 100 meshes to obtain the Jerusalem artichoke powder; and a preparation method of the *Poria cocos* water extract comprises: slicing fresh *Poria cocos*, drying the fresh *Poria cocos* slices at 70~80° C., and then crushing the dried *Poria cocos* slices; adding 10~15 times the mass of absolute ethanol, extracting for 2~4 h and subjecting the extract to filtering to obtain a residue; adding 8~10 times the mass of distilled water to the residue, heating and refluxing to extract for 2 h, filtering twice to obtain filtrates, combining the filtrates, subjecting the combined filtrate to concentrating and drying under reduced pressure to obtain the *Poria cocos* water extract.

4. The preparation method of claim 2, wherein in the freeze-drying step, a prefreezing process is carried out for 3 h at −80° C., and the mixed strain solution is quickly transferred to a vacuum freeze-drying machine for freeze-drying after being completely frozen; the freeze-drying conditions comprise a vacuum degree of 10 Pa and a cold trap temperature of −55° C.; and the frozen mixed strain solution is first heated at 10° C. for 2 hours, then heated up to 20° C. for 3 hours, and finally heated up to 30° C.; for a total duration of the vacuum freeze-drying process is 20 hours.

* * * * *